(12) United States Patent
Kato et al.

(10) Patent No.: US 11,925,324 B2
(45) Date of Patent: Mar. 12, 2024

(54) INSERTION APPARATUS AND ENDOSCOPE

(71) Applicant: OLYMPUS CORPORATION, Tokyo (JP)

(72) Inventors: Akihiro Kato, Hino (JP); Takuya Toyooka, Hachioji (JP); Fumitoshi Hayakawa, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 233 days.

(21) Appl. No.: 16/934,535

(22) Filed: Jul. 21, 2020

(65) Prior Publication Data

US 2020/0352421 A1 Nov. 12, 2020

Related U.S. Application Data

(63) Continuation of application No. PCT/JP2018/027626, filed on Jul. 24, 2018.

(30) Foreign Application Priority Data

Jan. 31, 2018 (JP) .................. 2018-015052

(51) Int. Cl.
*A61B 1/018* (2006.01)
*A61B 1/05* (2006.01)

(52) U.S. Cl.
CPC ................ *A61B 1/018* (2013.01); *A61B 1/05* (2013.01)

(58) Field of Classification Search
CPC .............. A61B 1/0008; A61B 1/00087; A61B 1/00089; A61B 1/00098; A61B 1/00101; A61B 1/018; A61B 1/012; A61B 1/00105; A61B 1/00103; A61B 1/00108; A61B 1/0011; A61B 1/00137; A61B 1/00119; A61B 1/00177; A61B 1/00179; A61B 1/0125; F16B 7/00; F16B 7/0406; F16B 7/0413; F16B 7/042; F16B 7/0426;
(Continued)

(56) References Cited

U.S. PATENT DOCUMENTS 4,669,471 A * 6/1987 Hayashi ......... A61B 17/320016
228/139
2015/0275946 A1* 10/2015 Ishizaki .................... F16D 1/06
403/359.1
(Continued)

FOREIGN PATENT DOCUMENTS

EP 3 097 843 A1 11/2016
JP S5934239 A * 2/1984 .............. F04B 37/14
(Continued)

OTHER PUBLICATIONS

English Translation of JPS5934239A (Year: 1984).*
(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An insertion apparatus includes: a base member, a rotary shaft, and a driven member including a hole. A plurality of concave portions are formed on the rotary shaft, and a pair of side wall surfaces which form each of the plurality of concave portions are disposed so as to intersect with each other at a right angle or at an obtuse angle.

22 Claims, 8 Drawing Sheets

(58) Field of Classification Search
CPC ...... F16B 7/044; F16B 7/0433; F16B 7/0446;
F16B 7/053; F16B 7/10
USPC ............................. 600/106–107, 170, 175
See application file for complete search history.

(56) References Cited

U.S. PATENT DOCUMENTS

| | | | |
|---|---|---|---|
| 2016/0270630 A1* | 9/2016 | Tanaka | A61B 1/00098 |
| 2016/0270634 A1* | 9/2016 | Tanaka | A61B 1/00098 |
| 2016/0367114 A1* | 12/2016 | Iizuka | A61B 1/00096 |
| 2018/0185045 A1* | 7/2018 | Ohki | A61B 1/00098 |
| 2019/0003522 A1* | 1/2019 | Bernard | B29C 70/30 |

FOREIGN PATENT DOCUMENTS

| | | | |
|---|---|---|---|
| JP | H08243076 A * | 9/1996 | ............... A61B 1/00 |
| JP | 2014-046167 A | 3/2014 | |
| WO | 2016/021231 A1 | 2/2016 | |

OTHER PUBLICATIONS

English Translation of JPH08243076A (Year: 1996).*
International Search Report dated Sep. 18, 2018 received in PCT/JP2018/027626.

* cited by examiner

INSERTION APPARATUS AND ENDOSCOPE

CROSS REFERENCE TO RELATED APPLICATION

This application is a continuation application of PCT/JP2018/027626 filed on Jul. 24, 2018 and claims benefit of Japanese Application No. 2018-015052 filed in Japan on Jan. 31, 2018, the entire contents of which are incorporated herein by this reference.

BACKGROUND OF THE INVENTION

1. Field of the Invention

The present invention relates to an insertion apparatus including an insertion section to be inserted into a subject and a driven member which is mounted on the insertion section, and an endoscope.

2. Description of the Related Art

As an insertion apparatus which has an insertion section to be inserted into a subject such as an endoscope or a medical treatment instrument, there has been known an insertion apparatus of a type which includes a movable driven member in the insertion section. For example, International Publication No. WO2016/021231 discloses an endoscope where an insertion section includes a raising base which is a rotatable driven member.

In the endoscope disclosed in International Publication No. WO2016/021231, a force which moves the raising base is transmitted to the raising base by way of a raising base operation arm which is connected to the raising base. The raising base and the raising base operation arm are connected to each other due to fitting engagement between a connection hole formed in the raising base and a shaft-shaped raising base connection portion mounted on the raising base operation arm. The connection hole and the raising base connection portion are respectively a hole and a shaft where an axis of rotation is set as a center axis. The connection hole and the raising base connection portion have an approximately triangular cross-sectional shape. In a state where the connection hole and the raising base connection portion fit each other, the relative rotation between both members is restricted.

SUMMARY OF THE INVENTION

According to one aspect of the present invention, there is provided an insertion apparatus which includes: a base member mounted on an insertion section to be inserted into a subject; a rotary shaft configured to rotate with respect to the base member; and a driven member including a hole which fits an outer periphery of the rotary shaft, the driven member being configured to be rotatably driven with respect to the base member by rotation of the rotary shaft, wherein the rotary shaft includes a plurality of concave portions formed along the outer periphery which is fitted in the hole, the concave portions being formed about an axis of the rotary shaft, and a pair of side wall surfaces which form each of the plurality of concave portions are arranged so as to intersect with each other at a right angle or at an obtuse angle.

According to another aspect of the present invention, there is provided an insertion apparatus which includes: a base member mounted on an insertion section to be inserted into a subject; a rotary shaft configured to rotate with respect to the base member; and a driven member including a hole which fits an outer periphery of the rotary shaft, the driven member configured to be rotatably driven with respect to the base member by rotation of the rotary shaft, wherein the rotary shaft includes a plurality of convex portions formed along the outer periphery which is fitted in the hole, the convex portions being formed about an axis of the rotary shaft, and among the plurality of convex portions, in a pair of convex portions disposed adjacently to each other, side wall surfaces on a side where the pair of convex portions are disposed adjacently to each other are arranged so as to intersect with each other at a right angle or at an obtuse angle.

According to yet another aspect of the present invention, there is provided an endoscope which includes: an image pickup apparatus disposed on a distal end portion of an insertion section to be inserted into a subject and having a direction of view on a side of the insertion section; a base member integrally fixed to the distal end portion; a rotary shaft configured to rotate with respect to the base member; and a driven member including a hole which fits an outer periphery of the rotary shaft, the driven member configured to be driven so as to rotate in the direction of view of the image pickup apparatus with respect to the base member by rotation of the rotary shaft, and the rotary shaft includes a plurality of concave portions on an outer periphery of the rotary shaft about an axis of the rotary shaft, and a pair of side wall surfaces which form each of the plurality of concave portions are disposed so as to intersect with each other at a right angle or at an obtuse angle.

DETAILED DESCRIPTION OF THE PREFERRED EMBODIMENT

Hereinafter, a preferred embodiment of the present invention is described with reference to drawings. In the respective drawings used in the description made hereinafter, to set sizes of the respective constitutional elements to a degree that allows the respective constitutional elements recognizable on the drawings, there may be a case where the magnification is made different for respective constitutional elements. The present invention is not limited to only the number of constitutional elements, shapes of the constitutional elements, ratios between sizes of the constitutional elements, and the relative positional relationship between the respective constitutional elements described in these drawings.

Figure 1:
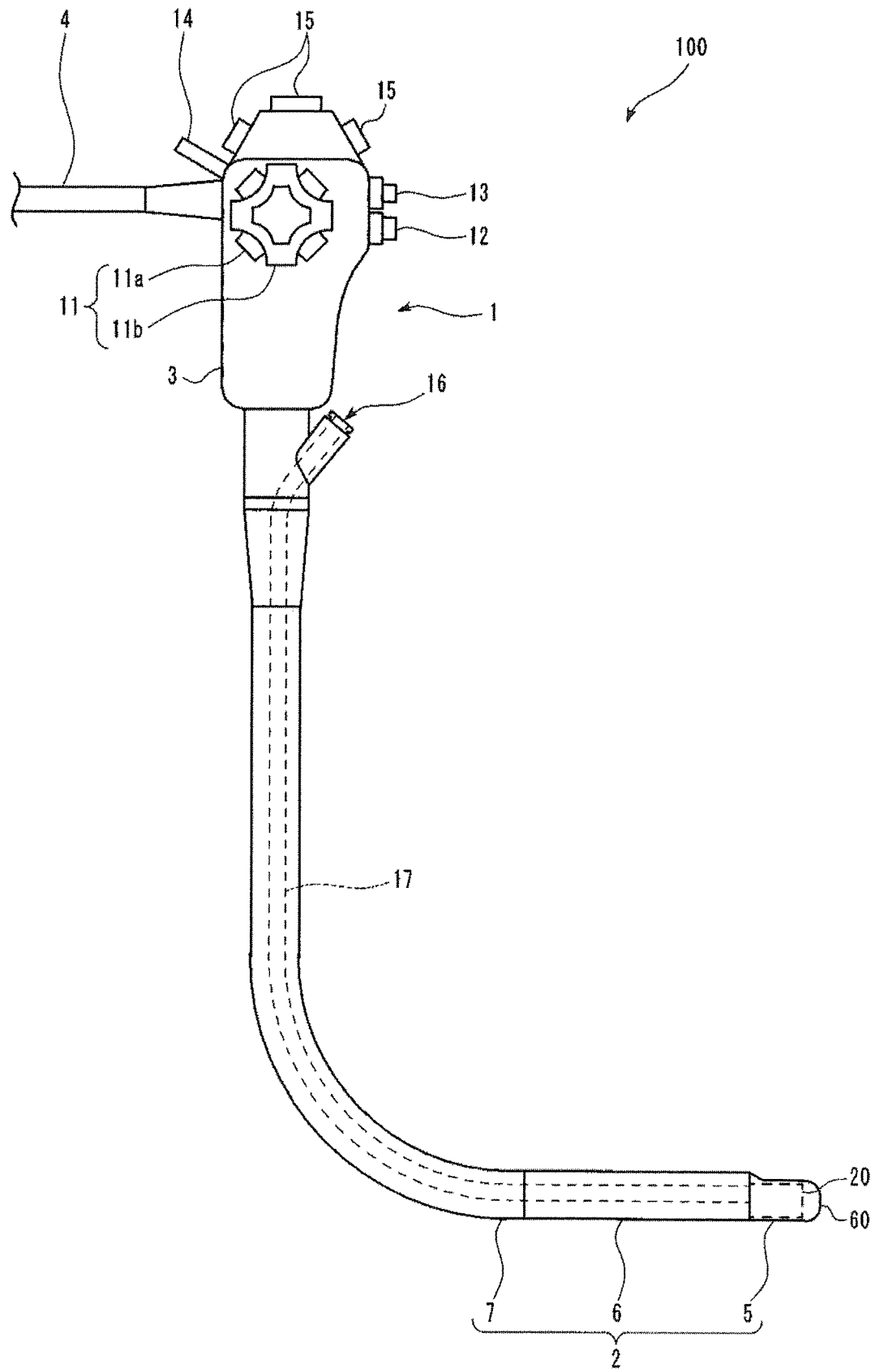
FIG. 1 is a view showing a schematic configuration of an insertion apparatus.

FIG. 1 is a view showing a schematic configuration of an insertion apparatus 100. The insertion apparatus 100 of this embodiment includes an insertion apparatus body 1 and a distal end cover 60. In this embodiment, as one example, the insertion apparatus 100 is an endoscope which has an insertion section 2 inserted into a human body which is a subject. More specifically, the insertion apparatus 100 is a side-viewing endoscope for intestine duodenum.

The insertion apparatus body 1 is formed of: the insertion section 2 to be inserted into a subject; an operation section 3 mounted on a proximal end side of the insertion section 2; and a universal cord 4 which extends from the operation section 3.

A bending operation device 11, an air/water feeding button 12, a suction button 13, a raising base operation lever 14, and operation switches 15 are mounted on the operation section 3. The operation switches 15 are electronic switches for operating an image pickup apparatus 42 (not shown in FIG. 1) mounted on the insertion section 2.

A treatment instrument insertion opening 16 through which a treatment instrument not shown in the drawing is introduced into a human body is formed in the operation section 3. A proximal end side of a channel tube 17 is connected to the treatment instrument insertion opening 16. A distal end side of the channel tube 17 opens at a distal end portion 5 of the insertion section 2.

The insertion section 2 is formed by connecting: the distal end portion 5 disposed on a distal end of the insertion section 2; a bending portion 6 which is disposed on a proximal end side of the distal end portion 5 and is bendable; and a flexible tube portion 7 which connects a proximal end side of the bending portion 6 and the operation section 3 to each other and has flexibility. The distal end cover 60 is mounted on the distal end portion 5. The configurations of the distal end portion 5 and the distal end cover 60 are described in detail later.

The bending portion 6 bends in an upward direction or in a downward direction corresponding to a rotation of a vertical bending knob 11a of the bending operation device 11 mounted on the operation section 3, and the bending portion 6 bends in a leftward direction or in a rightward direction corresponding to a rotation of a lateral bending knob 11b of the bending operation device 11.

A raising base operation wire 18 (not shown in FIG. 1) passes through the insertion section 2. The raising base operation wire 18 advances or retracts in a longitudinal direction corresponding to tilting of the raising base operation lever 14. The raising base operation lever 14 is an operation member with which a user operates a device for pushing or pulling the raising base operation wire 18.

A distal end of the raising base operation wire 18 is connected to a lever 51 described later (not shown in FIG. 1) which is mounted on the distal end portion 5. The insertion apparatus 100 may adopt a configuration where the raising base operation wire 18 is moved by a force which a user applies to the raising base operation lever 14, or may adopt a configuration where the raising base operation wire 18 is moved by a force which an electrically operated actuator generates.

Figure 2:
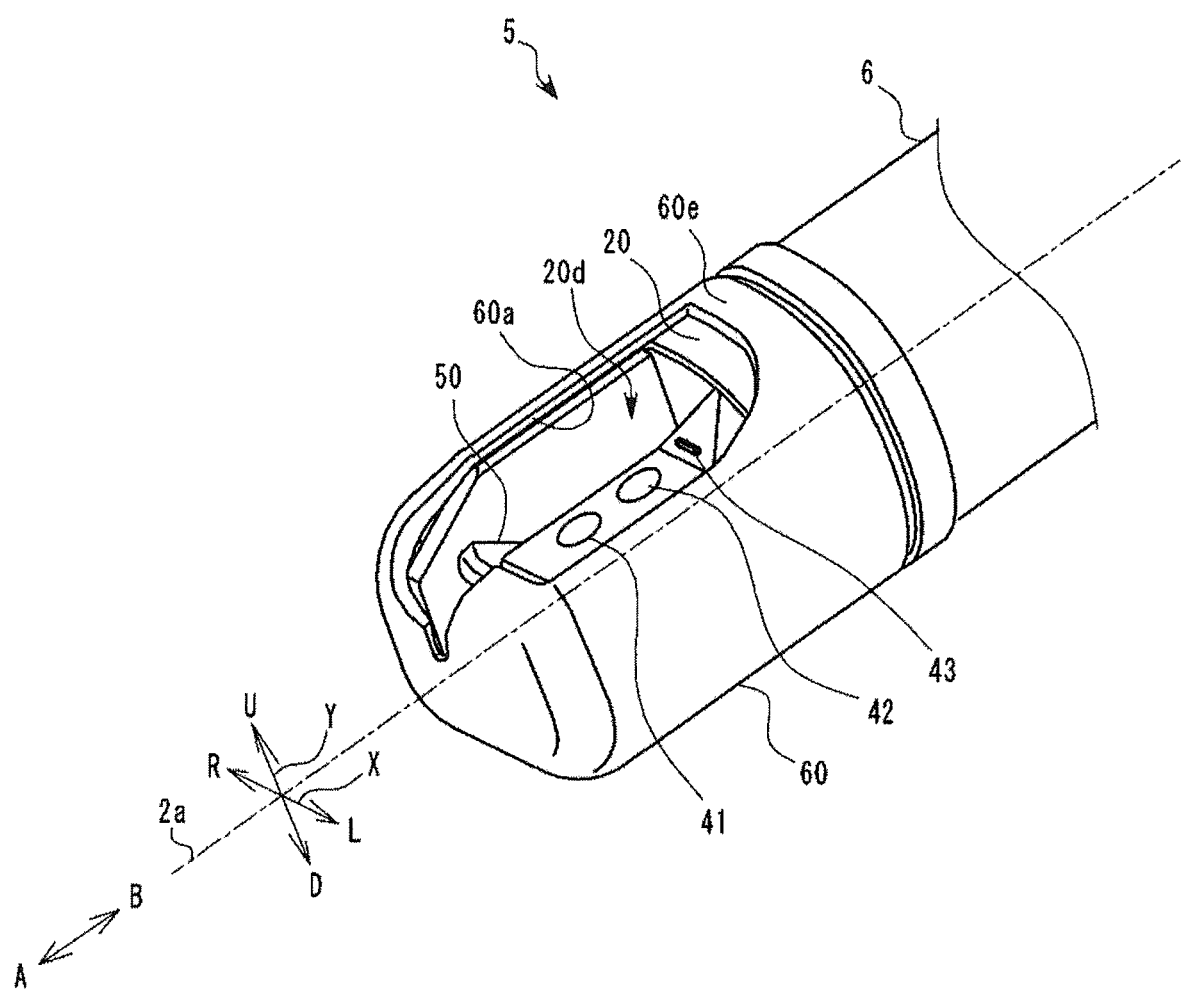
FIG. 2 is a perspective view of a distal end portion of an insertion section.
Figure 3:
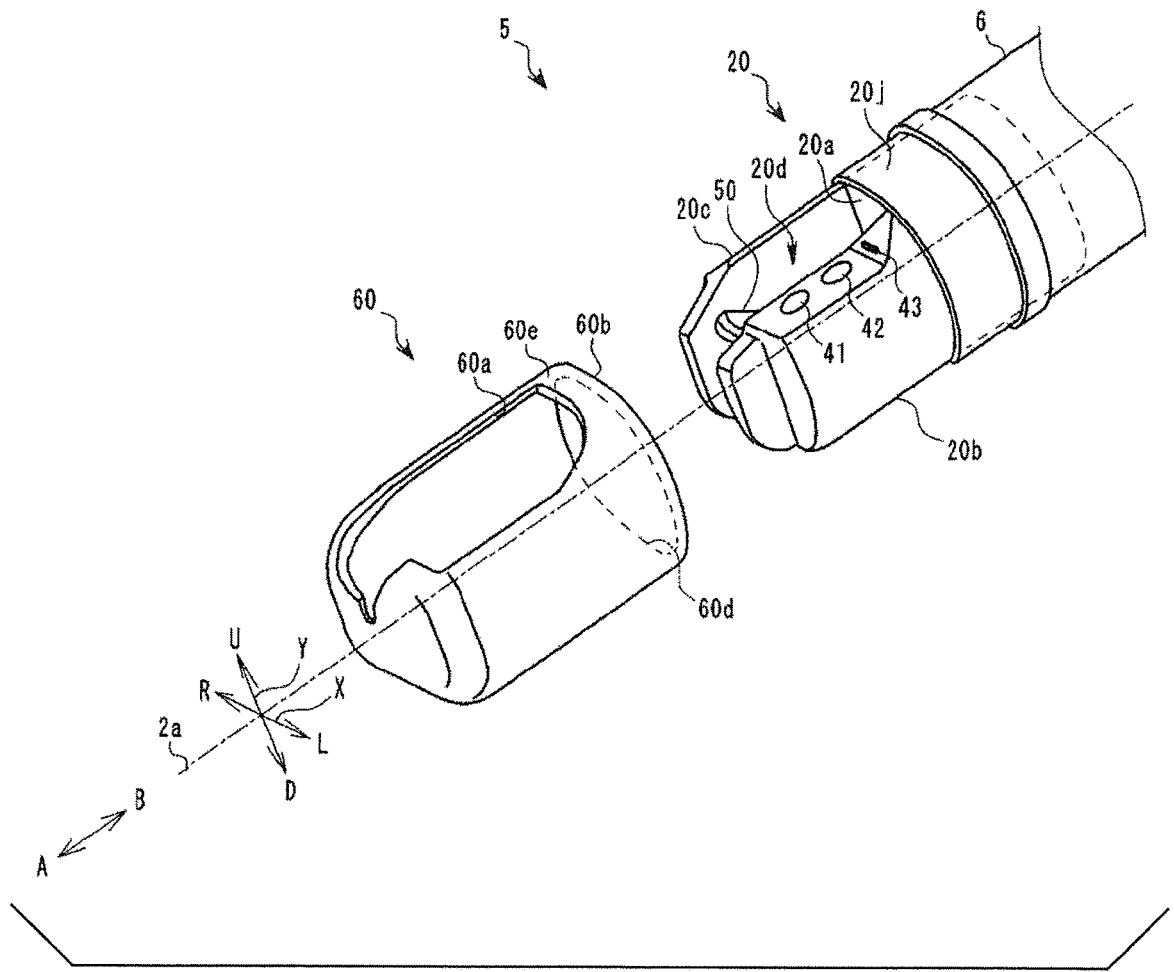
FIG. 3 is a perspective view showing a state where a distal end cover and a distal end member are separated from each other.
Figure 4:
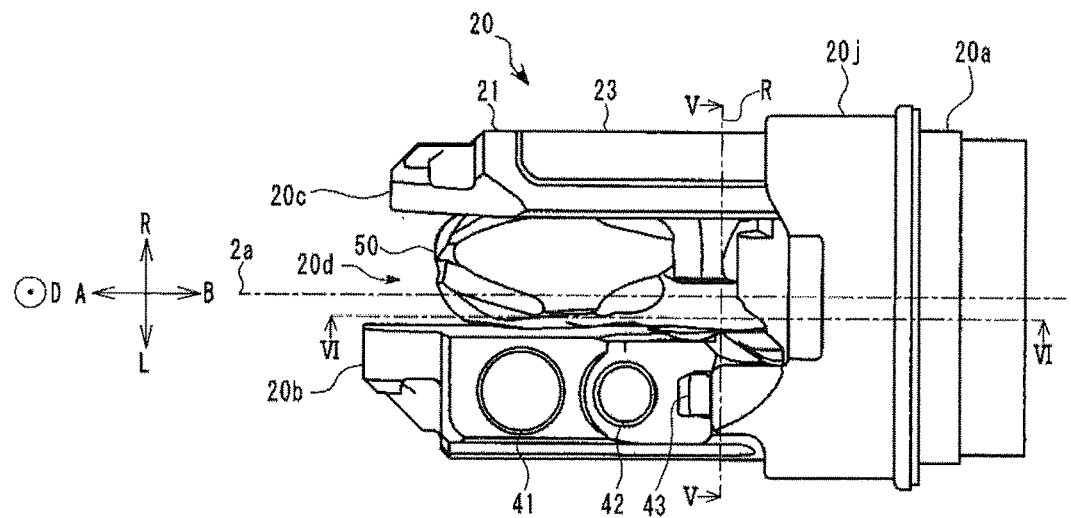
FIG. 4 is a view showing an upper surface of the distal end member.
Figure 5:
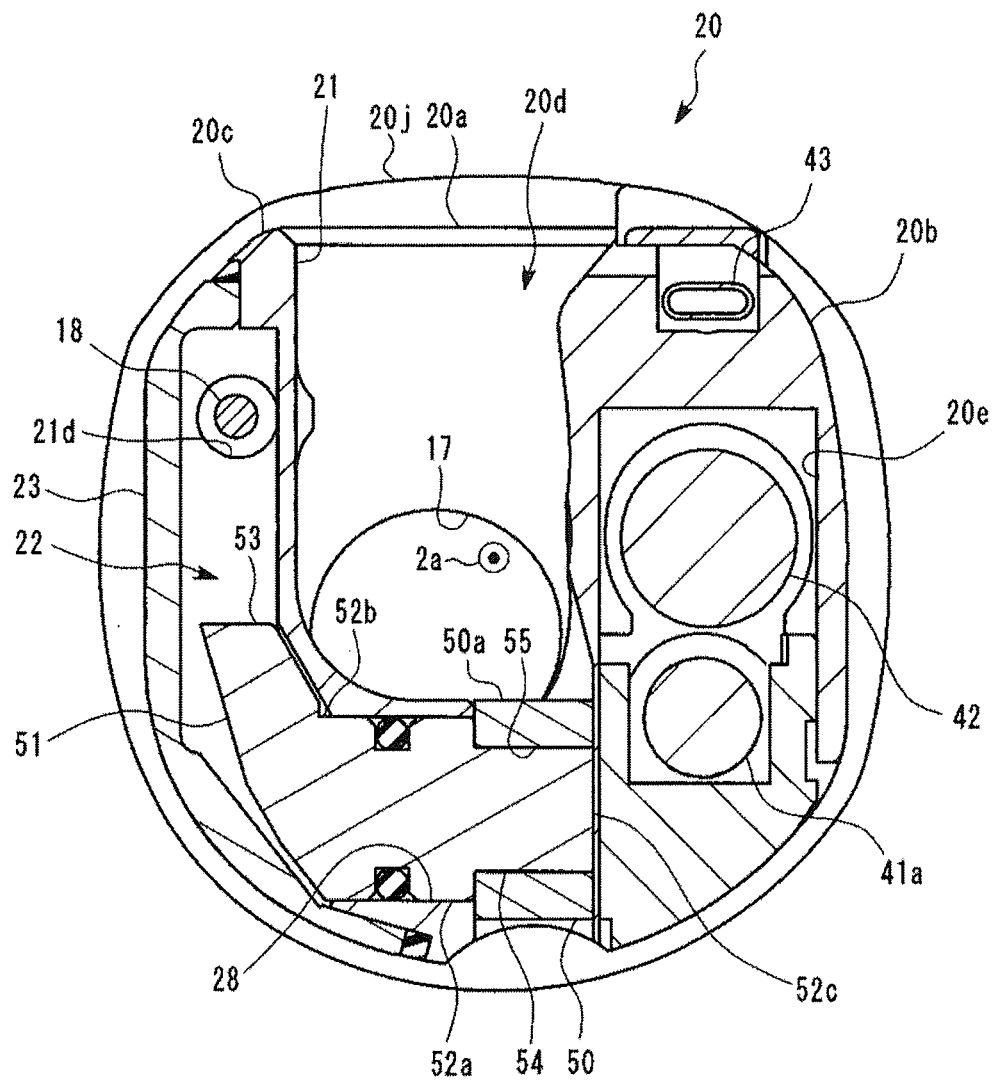
FIG. 5 is a cross-sectional view taken along line V-V in FIG. 4.
Figure 5:
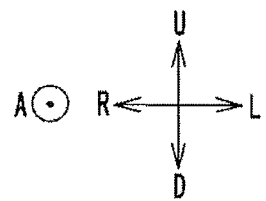
Figure 6:
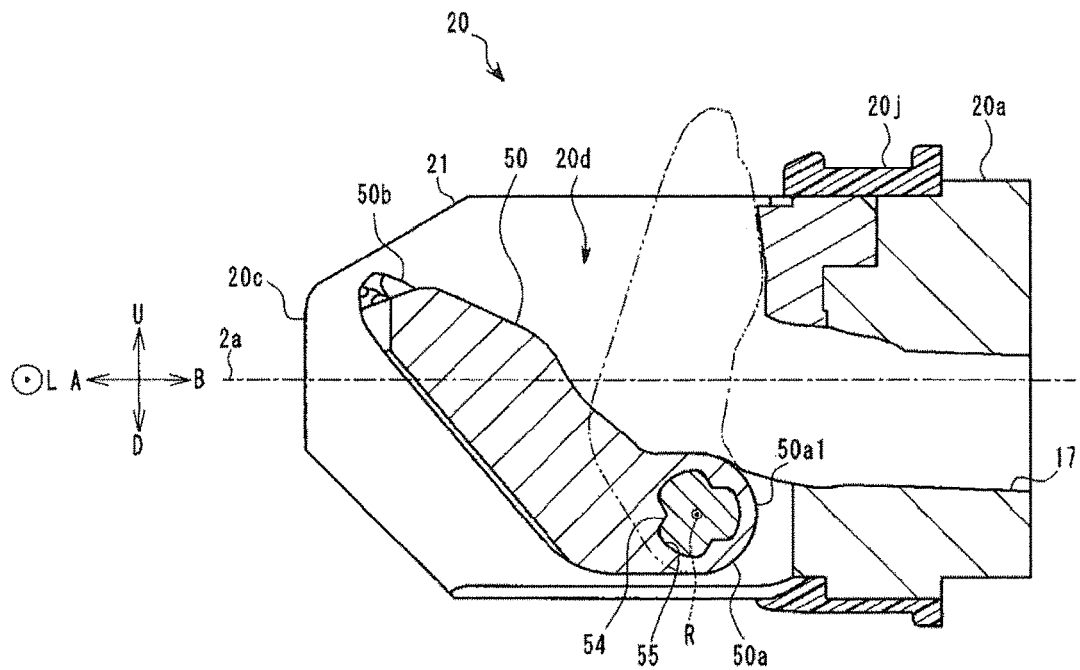
FIG. 6 is a cross-sectional view taken along line VI-VI in FIG. 4.

FIG. 2 is a perspective view of the distal end portion 5. As shown in FIG. 2, the distal end cover 60 is mounted on the distal end portion 5. The distal end cover 60 is a sheath-shaped member which covers a predetermined outer surface of the distal end portion 5, and is detachably mounted on the distal end portion 5. FIG. 3 is a perspective view showing a state where the distal end cover 60 and the distal end portion 5 are separated from each other. FIG. 4 is a view showing an upper surface of the distal end portion 5 in a state where the distal end cover 60 is not mounted on the distal end portion 5. FIG. 5 is a cross-sectional view taken along line V-V in FIG. 4. FIG. 6 is a cross-sectional view taken along line VI-VI in FIG. 4.

In this embodiment, as one example, the distal end cover 60 is formed using a resin which has low elasticity compared to rubber or the like and is easily plastically deformable and breakable among resins such as polyethylene or polypropylene. In this embodiment, the distal end cover 60 is formed such that irreversible deformation or breaking occurs in the distal end cover 60 when the distal end cover 60 is removed from the distal end portion 5 after the distal end cover 60 is mounted on the distal end portion 5. Accordingly, the distal end cover 60 cannot be reused. FIG. 3 shows the distal end cover 60 in a state where the distal end cover 60 has not ever been mounted on the distal end portion 5 (unused state).

The configuration of the distal end portion 5 is described. In the description made hereinafter, an axis which extends along a longitudinal axis of the elongated insertion section 2 is referred to as longitudinal axis 2a. A direction directed toward a distal end side of the insertion section 2 along the longitudinal axis 2a is referred to as a distal end direction A, and a direction opposite to the distal end direction A is referred to as a proximal end direction B. Two straight line axes which are orthogonal to each other on a plane orthogonal to the longitudinal axis 2a are defined as an X axis and a Y axis respectively. A direction directed toward one side along the X axis is referred to as a rightward direction R, and a direction opposite to the rightward direction R is referred to as a leftward direction L. A direction directed toward one side along the Y axis is referred to as an upward direction U, and a direction opposite to the upward direction U is referred to as a downward direction D. The X axis and the Y axis are substantially parallel to a bending direction of the bending portion 6. In this embodiment, as one example, in a case where the distal end portion 5 is viewed from a proximal end side toward a distal end side along the longitudinal axis 2a, and the X axis is taken horizontally, assume a right side as the rightward direction R and an upside as the upward direction U.

As shown in FIG. 3, the distal end portion 5 includes a distal end member 20 and an insulation portion 20j. The distal end member 20 has: a proximal portion 20a which is fixed to a distal end of the bending portion 6; a first arm portion 20b and a second arm portion 20c which form a pair of arm portions projecting from the proximal portion 20a in the distal end direction A; and a raising base accommodating space 20d which is a space formed between the first arm portion 20b and the second arm portion 20c. The proximal portion 20a has a substantially columnar profile.

The insulation portion 20j is an annular member which covers an outer periphery of the proximal portion 20a. The insulation portion 20j is made of a resin or ceramic having electric insulation property.

The first arm portion 20b and the second arm portion 20c are disposed such that the raising base accommodating space 20d which is the space formed between the first arm portion 20b and the second arm portion 20c opens in three directions consisting of the upward direction U, the downward direction D, and the distal end direction A. In other words, the first arm portion 20b and the second arm portion 20c are arranged in a direction along the X axis with the raising base accommodating space 20d sandwiched between the first arm portion 20b and the second arm portion 20c. In this embodiment, as one example, the first arm portion 20b is disposed on a leftward direction L side of the raising base accommodating space 20d, and the second arm portion 20c is disposed on a rightward direction R side of the raising base accommodating space 20d.

On an upper surface of an outer peripheral surface of the first arm portion 20b facing in the upward direction U, an illumination lens 41, the image pickup apparatus 42, and a cleaning nozzle 43 are disposed. The illumination lens 41 is provided for irradiating an illumination light toward an object, an image of which is picked up by the image pickup apparatus 42.

As shown in FIG. 5, an image pickup apparatus accommodating chamber 20e is formed in the first arm portion 20b. A distal end portion of an optical fiber cable 41a and the image pickup apparatus 42 are disposed in the image pickup apparatus accommodating chamber 20e. The optical fiber cable 41a passes through the insertion section 2, and guides an illumination light irradiated from a light emitting device to the illumination lens 41. The light emitting device may be disposed in the insertion apparatus 100, or may be disposed in an external apparatus connected to the insertion apparatus 100.

A field of view of the image pickup apparatus 42 is defined with the substantially upward direction U set as the center of the field of view. In other words, the image pickup apparatus 42 embraces a side of the insertion section 2 in the field of view. The cleaning nozzle 43 is a part which ejects a fluid toward the illumination lens 41 and the image pickup apparatus 42.

A lever chamber 22 in which the lever 51 is disposed is formed in the second arm portion 20c. The lever 51 is a member which transmits the movement of the raising base operation wire 18 to a driven member 50. The lever 51 and the driven member 50 are described in detail later.

The distal end cover 60 is a sheath-shaped member where a distal end direction A side is closed and a proximal end direction B side is opened. An opening formed on the proximal end direction B side of the distal end cover 60 is referred to as an insertion opening 60d. In mounting the distal end cover 60 on the distal end portion 5, the distal end portion 5 is inserted in the distal end cover 60 through the insertion opening 60d.

The distal end cover 60 has an opening portion 60a through which the raising base accommodating space 20d is exposed only in the upward direction U in a state where the distal end cover 60 is mounted on the distal end portion 5. The illumination lens 41, the image pickup apparatus 42, and the cleaning nozzle 43 are also exposed in the upward direction U through the opening portion 60a in a state where the distal end cover 60 is mounted on the distal end member 20.

On an outer surface of the distal end cover 60, the opening portion 60a is not connected with the insertion opening 60d. Accordingly, an annularly continuous annular portion 60e is formed on a proximal end 60b of the distal end cover 60 over the whole circumference about the longitudinal axis 2a. In a state where the distal end cover 60 is mounted on the distal end member 20, the annular portion 60e fits an outer periphery of the insulation portion 20j.

Next, the lever 51 and the driven member 50 disposed on the second arm portion 20c of the distal end member 20 are described in detail.

Figure 7:
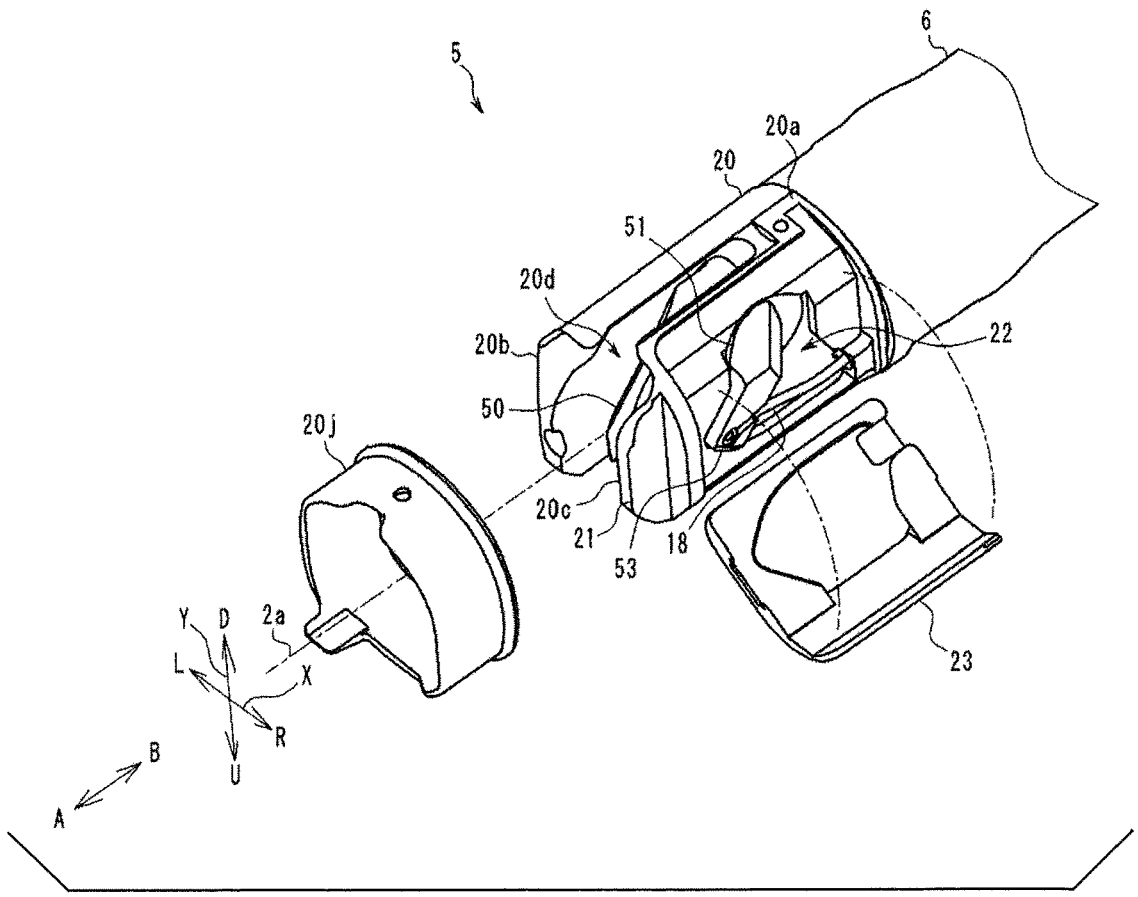
FIG. 7 is an exploded perspective view of the distal end member.
Figure 8:
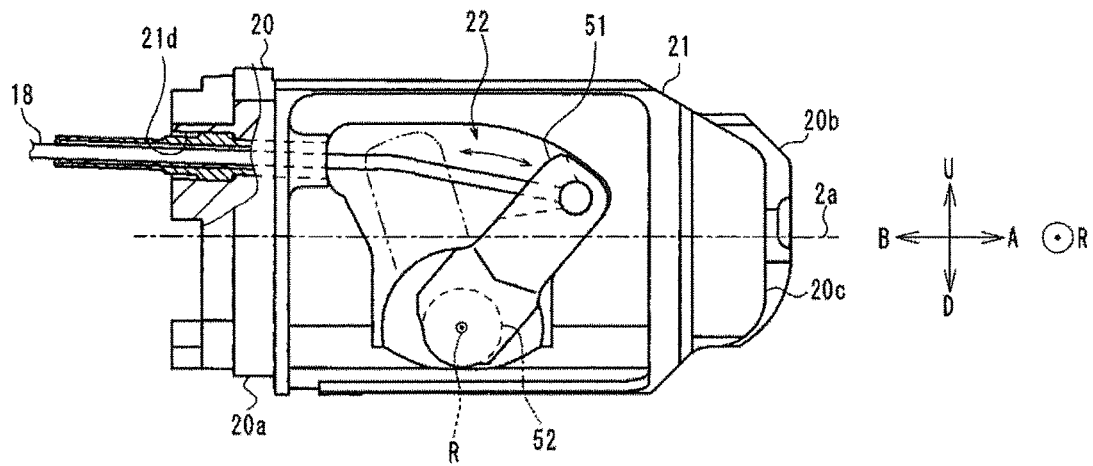
FIG. 8 is a view showing a right side surface of the distal end member in a state where a lid member is removed from the distal end member.
Figure 9:
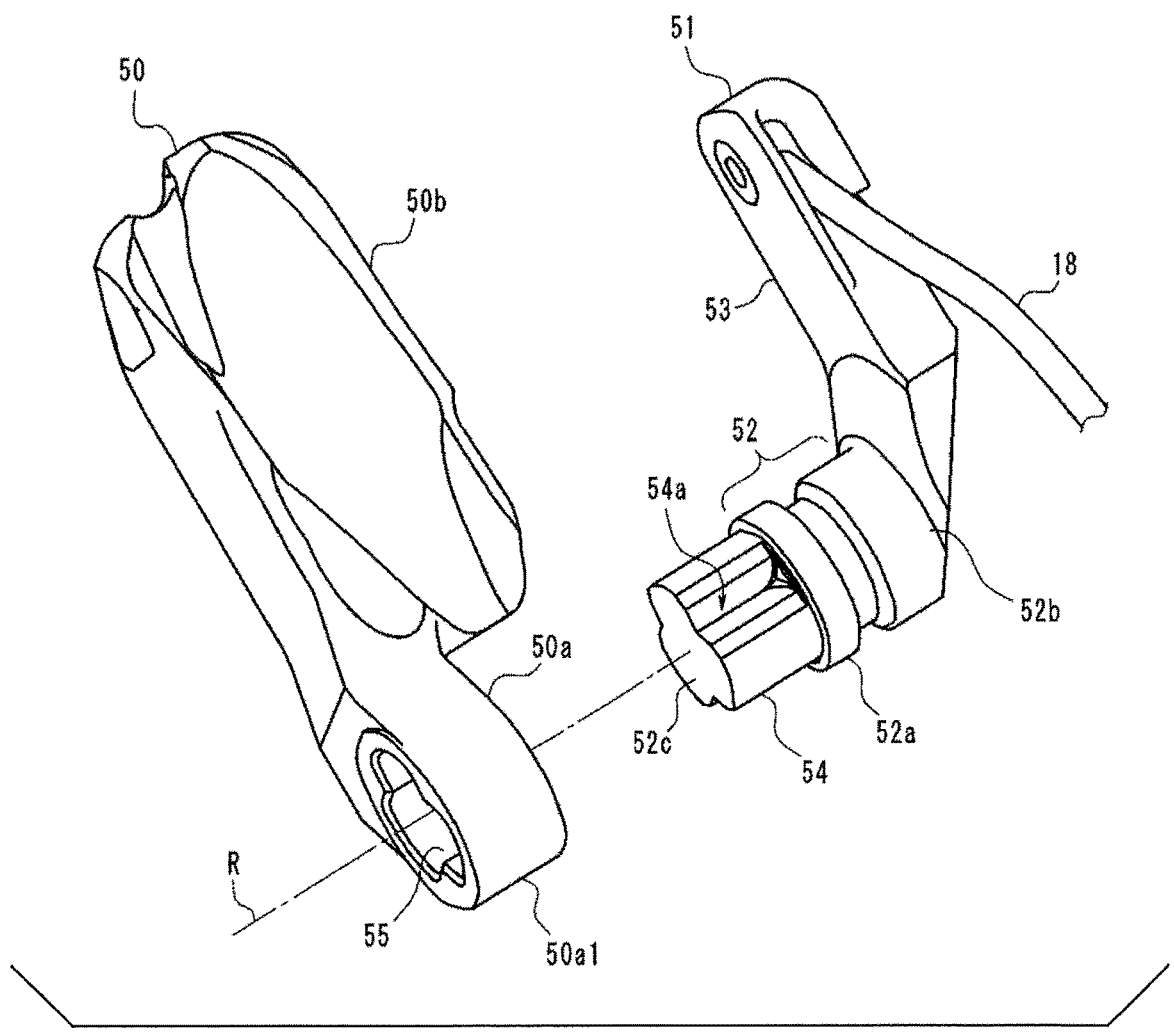
FIG. 9 is a perspective view of a lever and a driven member.

FIG. 7 is an exploded perspective view of the distal end member 20. FIG. 8 is a view showing a right side surface of the distal end member 20 in a state where the lid member 23 is removed from the distal end member 20. FIG. 9 is a perspective view of the lever 51 and the driven member 50.

As shown in FIG. 5 and FIG. 7, the second arm portion 20c is formed of a base member 21 which is integrally formed with the distal end member 20, and the lid member 23 which is fixed by adhesion to the base member 21 using an adhesive agent. In this embodiment, the lid member 23 is fixed to a left side surface of the base member 21. The lever chamber 22 is a space surrounded by the base member 21 and the lid member 23.

As shown in FIG. 8, the lever chamber 22 communicates with the inside of the bending portion 6 through a through hole 21d. The through hole 21d penetrates the base member 21 and the proximal portion 20a from an inside of the lever chamber 22 in the proximal end direction B. The raising base operation wire 18 passes through the through hole 21d. As described previously, the raising base operation wire 18 passes through the insertion section 2 including the bending portion 6.

The lever 51 is disposed in the lever chamber 22. As shown in FIG. 5, FIG. 8, and FIG. 9, the lever 51 includes a rotary shaft 52 and an arm portion 53.

The rotary shaft 52 is a columnar part which rotates with respect to the base member 21. A bearing 28 is formed in the base member 21 in a state where the bearing 28 penetrates from the inside of the lever chamber 22 to the raising base accommodating space 20d. The bearing 28 has a circular hole about a straight line axis R. In this embodiment, as one example, the straight line axis R is substantially parallel to the X axis.

The rotary shaft 52 has a circular columnar portion 52a having an outer diameter which allows fitting engagement of the circular columnar portion 52a with the bearing 28 with a predetermined gap formed between the circular columnar portion 52a and the bearing 28. The circular columnar portion 52a rotates in the bearing 28 relative to the base member 21 about the straight line axis R. The bearing 28 is a so-called slide bearing which rotatably supports the rotary shaft 52.

As shown in FIG. 9, the arm portion 53 is fixed to a first end portion 52b which forms an end of the rotary shaft 52 on a lever chamber 22 side. The arm portion 53 extends in the lever chamber 22 in a direction substantially orthogonal to the straight line axis R (that is, the center axis of the circular columnar portion 52a).

A distal end of the raising base operation wire 18 is connected to the arm portion 53 at a position spaced apart from the straight line axis R. As described previously, the raising base operation wire 18 advances or retracts in the longitudinal direction corresponding to tilting of the raising base operation lever 14. Along with advancing or retracting of the raising base operation wire 18, the lever 51 rotates about the straight line axis R. In other words, the lever 51 rotates about the straight line axis R corresponding to tilting of the raising base operation lever 14.

As shown in FIG. 5, a second end portion 52c which is an end of the rotary shaft 52 on a raising base accommodating space 20d side projects into the raising base accommodating space 20d from the base member 21. A fitting engagement shaft 54 is formed on the second end portion 52c. The fitting engagement shaft 54 is a shaft-shaped part which engages with the driven member 50. The fitting engagement shaft 54 has a columnar shape extending along the straight line axis R.

A fitting engagement hole 55 in which the fitting engagement shaft 54 is inserted is formed in the driven member 50. In a state where the fitting engagement shaft 54 is inserted into the fitting engagement hole 55, a rotation of the driven member 50 relative to the lever 51 about the straight line axis R is restricted. Accordingly, the driven member 50 rotates relative to the base member 21 about the straight line axis R together with the lever 51. The rotation of the driven member 50 relative to the lever 51 about the straight line axis R may be restricted with a slight play. Shapes of the fitting engagement shaft 54 and the fitting engagement hole 55 are described in detailed later.

As shown in FIG. 6 and FIG. 9, the driven member 50 includes a proximal end portion 50a in which the fitting engagement hole 55 is formed, and a tongue-shaped part 50b which extends from the proximal end portion 50a in a direction substantially orthogonal to the straight line axis R. The tongue-shaped part 50b extends in a direction substantially orthogonal to the straight line axis R in the raising base accommodating space 20d. The proximal end portion 50a includes a circular columnar shape portion 50a1 about the straight line axis R. In this embodiment, the circular columnar shape portion 50a1 is a portion of the proximal end portion 50a extending in the proximal end direction B from the straight line axis R, and the circular columnar shape portion 50a1 has a substantially semicircular columnar shape.

The treatment instrument channel tube 17 opens at a portion of the raising base accommodating space 20d on a proximal end direction B side of the driven member 50. The treatment instrument which projects from the treatment instrument channel tube 17 is brought into contact with a surface of the tongue-shaped part 50b of the driven member 50 facing in the upward direction U. Accordingly, along with the rotation of the driven member 50 about the straight line axis R, the treatment instrument projecting from the treatment instrument channel tube 17 bends, and a direction that the treatment instrument projects from the distal end portion 5 changes. The driven member 50 is referred to as a treatment instrument raising base or the like.

Figure 10:
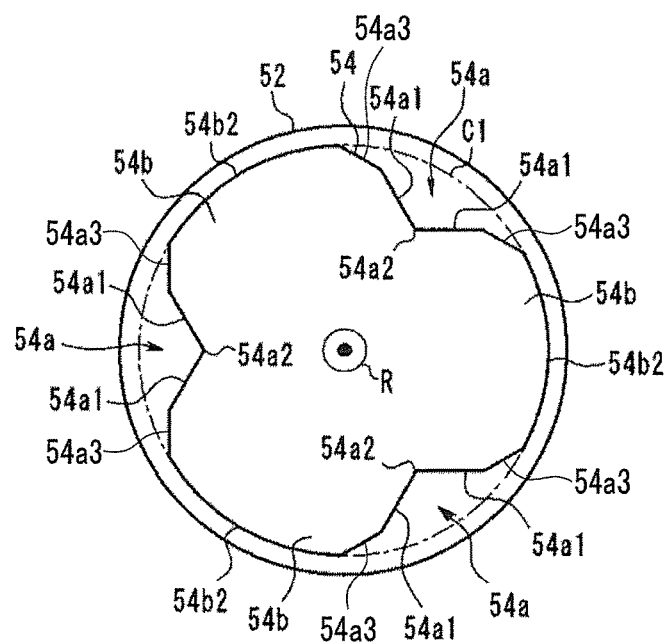
FIG. 10 is a view of a fitting engagement shaft as viewed in a direction parallel to a straight line axis R.
Figure 11:
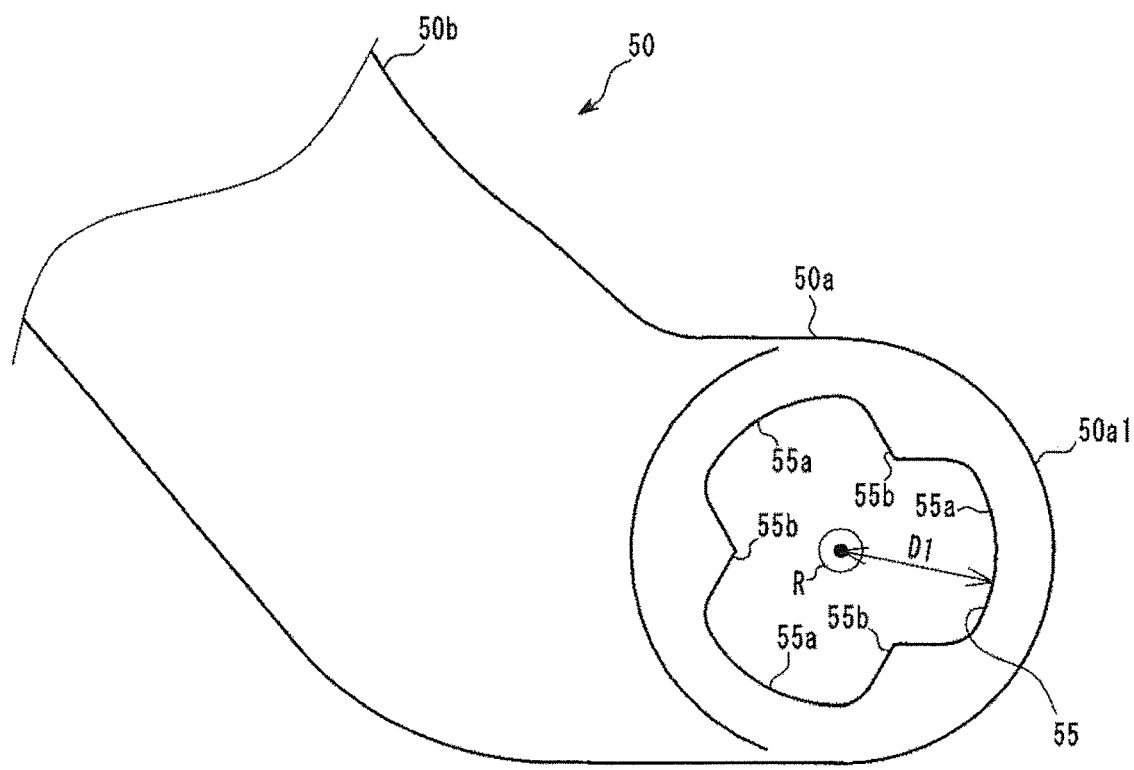
FIG. 11 is a view of a fitting engagement hole as viewed in a direction parallel to the straight line axis R.

Next, a shape of the fitting engagement shaft 54 formed on the rotary shaft 52 and a shape of the fitting engagement hole 55 formed in the driven member 50 are described. In this embodiment, the fitting engagement shaft 54 and the fitting engagement hole 55 are characterized in a cross-sectional shape on a plane orthogonal to the straight line axis R. FIG. 10 is a view of the fitting engagement shaft 54 as viewed in a direction parallel to the straight line axis R. FIG. 11 is a view of the fitting engagement hole 55 as viewed in a direction parallel to the straight line axis R.

As described previously, the fitting engagement shaft 54 and the fitting engagement hole 55 restrict the rotation of the driven member 50 about the straight line axis R relative to the lever 51 in a state where the fitting engagement shaft 54 and the fitting engagement hole 55 engage with each other. In this embodiment, by forming concaves and convexes which engage with each other on the fitting engagement shaft 54 and in the fitting engagement hole 55 in a circumferential direction, the rotation of the driven member 50 about the straight line axis R relative to the lever 51 is restricted.

More specifically, the fitting engagement shaft 54 has three or four concave portions 54a disposed in a juxtaposed manner on an outer periphery of the fitting engagement shaft 54 along the circumferential direction about the straight line axis R. In such a configuration, the concave portion indicates, as shown in FIG. 10, a portion having a shape indented inwardly in a radial direction from an imaginary circle C1 about the straight line axis R on a plane orthogonal to the straight line axis R. Further, as shown in FIG. 9 and FIG. 10, the concave portion 54a is a portion having a groove shape extending parallel to the straight line axis R on the outer periphery of the fitting engagement shaft 54.

Assume a portion of the concave portion 54a closest to the straight line axis R as a bottom portion 54a2. The concave portion 54a has a pair of side wall surfaces 54a1 which face each other with the bottom portion 54a2 sandwiched between the side wall surfaces 54a1 in a cross section orthogonal to the straight line axis R. The side wall surfaces 54a1 are surfaces which are directed substantially outwardly in the radial direction from the bottom portion 54a2.

Portions of the fitting engagement shaft 54 each of which is sandwiched by a pair of concave portions 54a disposed adjacently to each other on an outer periphery of the fitting engagement shaft 54 form the convex portions 54b which protrude toward the outside in the radial direction relative to the bottom portions 54a2 of the concave portions 54a. In other words, the fitting engagement shaft 54 has three or four convex portions 54b disposed in a juxtaposed manner along the circumferential direction on the outer periphery of the fitting engagement shaft 54 about the straight line axis R.

In the above-mentioned configuration, assume a portion of the convex portion 54b remotest from the straight line axis R as a vertex portion 54b2. Each side wall surface 54a1 of the concave portion 54a forms a portion of an inclined surface extending from the vertex portion 54b2 of the convex portion 54b to the bottom portion 54a2 of the concave portion 54a.

The fitting engagement hole 55 is a hole having a substantially same shape as the fitting engagement shaft 54. A fitting engagement relationship between the fitting engagement shaft 54 and the fitting engagement hole 55 may be a so-called clearance fit where a predetermined gap is formed between the fitting engagement shaft 54 and the fitting engagement hole 55, or may be a so-called close fit where a press-fitting relationship is established between the fitting engagement shaft 54 and the fitting engagement hole 55. In this embodiment, as one example, the fitting engagement relationship between the fitting engagement shaft 54 and the fitting engagement hole 55 is a clearance fit.

In an actual configuration, to realize the clearance fit relationship, a gap (so-called relief) which allows irregularities in size is formed on either one of the fitting engagement shaft 54 and the fitting engagement hole 55 or on both the fitting engagement shaft 54 and the fitting engagement hole 55. However, the description of such a gap is omitted.

More specifically, in this embodiment, the fitting engagement shaft 54 has three concave portions 54a. In other words, fitting engagement shaft 54 has three convex portions 54b.

In this embodiment, three concave portions 54a are arranged at an equal interval of 120 degrees in the circumferential direction about the straight line axis R. Further, three concave portions 54a are formed in a shape where three concave portions 54a are arranged in point symmetry with respect to the straight line axis R on a cross section formed of a plane orthogonal to the straight line axis R. Accordingly, in this embodiment, three convex portions 54b are arranged at equal interval of 120 degrees in the circumferential direction about the straight line axis R. Further, three convex portions 54b are formed in a shape where three convex portions 54b are arranged in point symmetry with respect to the straight line axis R in a cross section formed of a plane orthogonal to the straight line axis R. These shapes are not limited to such a point symmetrical shape. For example, the shapes may adopt a line symmetrical shape or may not adopt a symmetrical shape.

The vertex portions 54b2 of three convex portions 54b inscribe the imaginary circle C1 about the straight line axis R. The vertex portions 54b2 of three convex portions 54b respectively include a cylindrical outer peripheral surface which agrees with the imaginary circle C1 in a cross section formed of a plane orthogonal to the straight line axis R.

The side wall surfaces 54a1 which face each other with the bottom portion 54a2 of the concave portion Ma sandwiched between the side wall surfaces 54a1 respectively is a plane parallel to the straight line axis R. Flat surfaces 54a3 formed on the side wall surfaces 54a1 are spaced apart from a plane which includes the straight line axis R.

In the cross section formed of the plane orthogonal to the straight line axis R, an angle made by the pair of flat surfaces 54a3 which each concave portion Ma has is a right angle or an obtuse angle. In other words, in the cross section formed of the plane orthogonal to the straight line axis R, the angle made by the pair of flat surfaces 54a3 which each concave portion Ma has is 90 degrees or more. In this embodiment, the angle made by the pair of flat surfaces 54a3 is an angle made by the pair of flat surfaces 54a3 which intersect with each other on the outer peripheral surface of the fitting engagement shaft 54.

In other words, the pair of side wall surfaces 54a1 which the pair of convex portions 54b disposed adjacently to each other include and face with each other include the flat surfaces 54a3 which intersect with each other at a right angle or at an obtuse angle on the outer peripheral surface of the fitting engagement shaft 54.

An inner peripheral surface of the fitting engagement hole 55 includes: a circular cylindrical surface 55a which has a predetermined radius D1 about the straight line axis R; and has three or four engaging projections 55b which project inwardly in a radial direction from the circular cylindrical surface 55a.

A radius D1 of the circular cylindrical surface 55a is a value which allows a circular cylinder which is brought into contact with all vertex portions 54b2 of three convex portions 54b to be fitted in the circular cylindrical surface 55a. In other words, the radius D1 of the circular cylindrical surface 55a is a value which allows the imaginary circle C1 to be fitted in the circular cylindrical surface 55a with a clearance fit relationship. Due to the fitting engagement between the circular cylindrical surface 55a of the fitting engagement hole 55 and the vertex portions 54b2 of the fitting engagement shaft 54, the driven member 50 is positioned with respect to the lever 51 in a direction orthogonal to the straight line axis R.

The engaging projections 55b project into all concave portions 54a in a state where the fitting engagement shaft 54 is fitted in the fitting engagement hole 55. In other words, in this embodiment, three engaging projections 55b are arranged at an equal interval of 120 degrees in a circumferential direction about the straight line axis R. By allowing the engaging projections 55b to project into the concave portions 54a, the driven member 50 is positioned with respect to the lever 51 about the straight line axis R.

As described previously, the portion of the driven member 50 where the fitting engagement hole 55 is formed includes the circular columnar shape portion 50a1 which forms the profile having the center axis on the straight line axis R. In this embodiment, three engaging projections 55b are arranged at the positions where these engaging projections 55b overlap with the circular columnar shape portion 50a1 in the circumferential direction about the straight line axis R.

Portions of the circular columnar shape portion 50a1 where the engaging projections 55b are arranged have a larger wall thickness than portions of the circular columnar shape portion 50a1 where the circular cylindrical surface 55a is arranged. In such a configuration, "wall thickness" means a thickness of the driven member 50 in the radial direction about the straight line axis R.

As has been described heretofore, the insertion apparatus 100 according to this embodiment includes: the rotary shaft 52 which rotates about the straight line axis R with respect to the base member 21 which is mounted on the insertion section 2; and the driven member 50 which is connected to the rotary shaft 52 and rotates about the straight line axis R together with the rotary shaft 52. A force which rotates the rotary shaft 52 about the straight line axis R is applied to the rotary shaft 52 along with advancing or retracting of the raising base operation wire 18. The force which rotates the rotary shaft 52 is transmitted to the driven member 50 at portions where the side wall surfaces 54a1 of the fitting engagement shaft 54 and the engaging projections 55b of the fitting engagement hole 55 are brought into contact with each other.

The portions of the fitting engagement hole 55 where the engaging projections 55b are disposed are the portions where the driven member 50 has a large wall thickness and hence, the driven member 50 exhibits high rigidity and high strength against a force applied to the rotary shaft 52 which rotates the driven member 50 relative to the rotary shaft 52 about the straight line axis R. With such a configuration, according to the insertion apparatus 100 of this embodiment, when a force which rotates the driven member 50 relative to the rotary shaft 52 about the straight line axis R is applied to the rotary shaft 52, it is possible to suppress a deformation amount of the fitting engagement hole 55. The angle which the pair of flat surfaces 54a3 which each concave portion 54a formed on the rotary shaft 52 make is a right angle or an obtuse angle and hence, the concave portions 54a can be easily formed by working. In other words, according to the insertion apparatus 100 of this embodiment, workability and strength of the connection structure between the driven member 50 and the rotary shaft 52 for transmitting a force to the driven member 50, both of which are mounted on the insertion section 2, can be enhanced.

Figure 12:
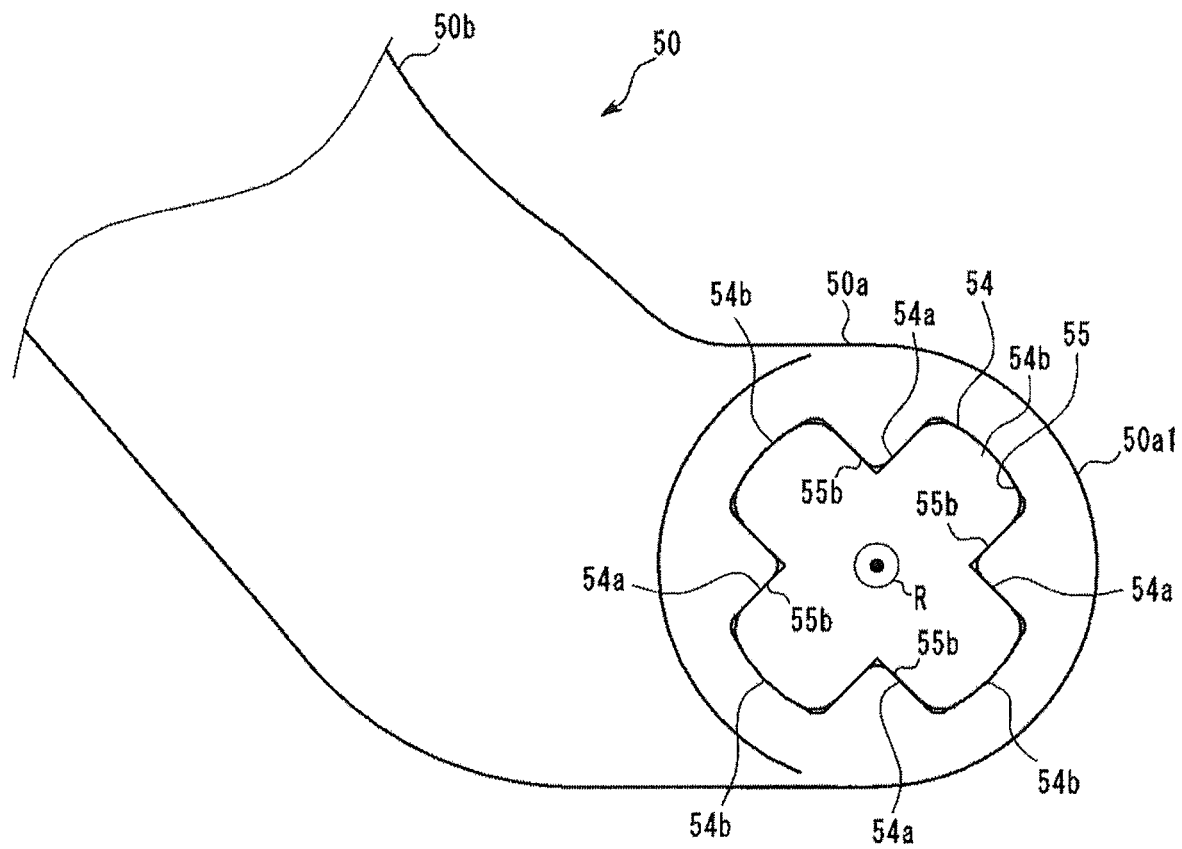
FIG. 12 is a view showing a modification of the fitting engagement shaft and the fitting engagement hole.

FIG. 12 shows a modification of this embodiment. As shown in FIG. 12, the number of concave portions 54a formed on a fitting engagement shaft 54 and the number of engaging projections 55b formed in a fitting engagement hole 55 may be four respectively. In this case, side wall surfaces 54a1 which face each other in the concave portion 54a have an orthogonal relationship. Also in the modification shown in FIG. 12, a driven member 50 has a large wall thickness at portions of the fitting engagement hole 55 where engaging projections 55b are formed.

Accordingly, also in an insertion apparatus 100 of the modification shown in FIG. 12, strength of the connection structure between the driven member 50 and a rotary shaft 52 for transmitting a force to the driven member 50, both of which are mounted on the insertion section 2, can be enhanced.

Although the fitting engagement shaft 54 and the fitting engagement hole 55 are fitted each other by a clearance fit relationship, it is possible to partially or wholly eliminate a gap between the fitting engagement shaft 54 and the fitting engagement hole 55 by plastically deforming at least one of the fitting engagement shaft 54 and the fitting engagement hole 55 after both members are fitted each other.

For example, after the fitting engagement shaft 54 and the fitting engagement hole 55 are fitted each other, a force which collapses the proximal end portion 50*a* of the driven member 50 is applied to the proximal end portion 50*a* both in the upward direction U and in downward direction D so that the proximal end portion 50*a* is plastically deformed together with the fitting engagement hole 55. Due to the plastic deformation of the proximal end portion 50*a* and a change in shape of the fitting engagement hole 55 brought about by such plastic deformation of the proximal end portion 50*a*, a gap between the fitting engagement shaft 54 and the fitting engagement hole 55 is partially or wholly eliminated. By partially or wholly eliminating the gap between the fitting engagement shaft 54 and the fitting engagement hole 55, it is possible to eliminate a play at the connection portion between the lever 51 and the driven member 50.

In this embodiment, the raising base accommodating space 20*d* opens in the upward direction U and in the downward direction D. Accordingly, it is possible to easily apply a force for collapsing the proximal end portion 50*a* of the driven member 50 to the driven member 50 both in the upward direction U and in the downward direction D. A flat surface portion may be formed on the proximal end portion 50*a* of the driven member 50 for enabling easy applying of a force to the driven member 50 using a tool at the time of plastically deforming the driven member 50.

Further, for example, after fitting the fitting engagement shaft 54 and the fitting engagement hole 55 each other, a force which compresses the fitting engagement shaft 54 in a direction parallel to the straight line axis R may be applied to the fitting engagement shaft 54. With such an operation, the fitting engagement shaft 54 can be plastically deformed such that fitting engagement shaft 54 is shortened along the straight line axis R and a diameter of the fitting engagement shaft 54 is enlarged in the radial direction. By enlarging the diameter of the fitting engagement shaft 54 in the radial direction, a gap between the fitting engagement shaft 54 and the fitting engagement hole 55 is partially or wholly eliminated. By eliminating the gap between the fitting engagement shaft 54 and the fitting engagement hole 55, it is possible to eliminate a play at the connection portion between the lever 51 and the driven member 50.

The present invention is not limited to the above-mentioned embodiment, and the present invention can be suitably carried out with modifications without departing from the gist or idea of the present invention which can be read from the claims and the entire specification, and insertion apparatuses with such modification are also embraced in the technical scope of the present invention.

What is claimed is:

1. An insertion apparatus comprising:
   a base member mounted on an insertion section configured to be inserted into a subject;
   a rotary shaft configured to rotate relative to the base member; and
   a raising base including a hole having an inner periphery, the rotary shaft being disposed within the hole to fix an outer periphery of the rotary shaft relative to the inner periphery of the hole such that the raising base is rotatably driven with respect to the base member by rotation of the rotary shaft when the rotary shaft is disposed within the hole, wherein
   the rotary shaft includes a plurality of concave portions formed along the outer periphery, the concave portions being formed radially inward relative to a rotation axis of the rotary shaft,
   each of the plurality of concave portions having a pair of side wall surfaces disposed symmetrically relative to a plane passing through the rotation axis of the rotary shaft, the pair of side wall surfaces being arranged so as to be at a right angle relative to each other or being arranged so as to be at an obtuse angle relative to each other.

2. The insertion apparatus according to claim 1, wherein the rotary shaft is connected to a wire which passes through the insertion section, the rotary shaft being configured to rotate along with advancing or retracting of the wire in a longitudinal direction.

3. The insertion apparatus according to claim 1, wherein the raising base is a treatment instrument raising base disposed at a distal end portion of the insertion section.

4. The insertion apparatus according to claim 1, wherein the raising base includes: a proximal end portion in which the hole is formed; and a tongue-shaped part which extends from the proximal end portion in a direction orthogonal to the rotary shaft.

5. The insertion apparatus according to claim 1, wherein the insertion apparatus is configured such that a gap between the outer periphery of the rotary shaft and the inner periphery of the hole is partially or wholly eliminated due to plastic deformation of at least one of the rotary shaft and the raising base after fitting the rotary shaft and the hole to each other.

6. The insertion apparatus according to claim 5, wherein a proximal end portion of the raising base in which the hole is formed comprises a flat surface configured to plastically deform when the rotary shaft is fitted in the hole.

7. The insertion apparatus according to claim 1, wherein the inner periphery of the hole comprises a plurality of projections each configured to engage with a corresponding concave portion of the plurality of concave portions.

8. The insertion apparatus according to claim 1, wherein the inner periphery of the hole is defined by a plurality of circular cylindrical surfaces and a projection disposed between adjacent circular cylindrical surfaces of the plurality of circular cylindrical surfaces, each projection projecting radially from the adjacent circular cylindrical surfaces to engage with a corresponding concave portion of the plurality of concave portions.

9. The insertion apparatus according to claim 8, wherein the engaging projections having a surface area on which a rotating force is applied from the rotary shaft.

10. The insertion apparatus according to claim 1, wherein each of the plurality of concave portions having the pair of side wall surfaces, each side wall surface of the pair of side wall surfaces facing in a direction having a radial component, the radial component being less than being fully facing a radial direction, the pair of side wall surfaces being arranged so as to meet at a right angle or being arranged so as to meet at an obtuse angle.

11. The insertion apparatus according to claim 1, wherein the outer periphery between adjacent concave portions of the plurality of concave portions includes an outermost circumferential surface having a first length in a circumferential direction,
   each of the pair of side wall surfaces has a continuous second length, and the first length is longer than the second length.

12. An endoscope comprising:
an image pickup apparatus disposed on a distal end portion of an insertion section configured to be inserted into a subject, the image pickup apparatus having a direction of view on a side of the insertion section;
a base member integrally fixed to the distal end portion;
a rotary shaft configured to rotate relative to the base member; and
a raising base including a hole having an inner periphery, the rotary shaft being disposed within the hole to fix an outer periphery of the rotary shaft relative to the inner periphery of the hole such that the raising base rotates in the direction of view of the image pickup apparatus with respect to the base member by rotation of the rotary shaft when the rotary shaft is disposed within the hole, and
the rotary shaft includes a plurality of concave portions on an outer periphery of the rotary shaft, the concave portion being formed radially inward relative to a rotation axis of the rotary shaft,
each of the plurality of concave portions having a pair of side wall surfaces disposed symmetrically relative to a plane passing through the rotation axis of the rotary shaft, the pair of side wall surfaces being disposed so as to be at a right angle relative to each other or disposed so as to be an obtuse angle relative to each other.

13. The endoscope according to claim 12, wherein the rotary shaft is connected to a wire which passes through the insertion section, the rotary shaft being configured to rotate along with advancing or retracting of the wire in a longitudinal direction.

14. The endoscope according to claim 12, wherein the raising base is disposed at the distal end portion of the insertion section.

15. The endoscope according to claim 12, wherein the raising base includes: a proximal end portion in which the hole is formed; and a tongue-shaped part which extends from the proximal end portion in a direction orthogonal to the rotary shaft.

16. The endoscope according to claim 12, wherein the insertion apparatus is configured such that a gap between the outer periphery of the rotary shaft and the inner periphery of the hole is partially or wholly eliminated due to plastic deformation of at least one of the rotary shaft and the raising base after fitting the rotary shaft and the hole to each other.

17. The endoscope according to claim 16, wherein a proximal end portion of the raising base in which the hole is formed comprises a flat surface configured to plastically deform when the rotary shaft is fitted in the hole.

18. The endoscope according to claim 12, wherein the inner periphery of the hole comprises a plurality of projections each configured to engage with a corresponding concave portion of the plurality of concave portions.

19. The endoscope according to claim 12, wherein the inner periphery of the hole is defined by a plurality of circular cylindrical surfaces and a plurality of engaging projections disposed between each of the plurality of engaging projections, each of the engaging projections projecting radially from each of the plurality of circular cylindrical surfaces.

20. The endoscope according to claim 19, wherein the engaging projections having a surface area on which a rotating force is applied from the rotary shaft.

21. An insertion apparatus comprising:
a distal end portion;
a rotary shaft configured to rotate with respect to the distal end portion around an axis of the rotary shaft, the rotary shaft including a plurality of concave portions on an outer periphery of the rotary shaft, each concave portion of the plurality of concave portions being formed by a pair of side wall surfaces formed along the axis, each of the pair of side wall surfaces disposed symmetrically relative to a plane passing through a rotation axis of the rotary shaft so as to be at a right angle relative to each other or be at an obtuse angle relative to each other; and
a raising base including a hole having an inner periphery, the rotary shaft being disposed within the hole to fix the outer periphery of the rotary shaft relative to the inner periphery of the hole such that the raising base is rotatably driven with respect to the distal end portion by rotation of the rotary shaft when the rotary shaft is disposed within the hole.

22. The insertion apparatus according to claim 21, wherein the inner periphery of the hole comprises a plurality of projections each configured to engage with a corresponding concave portion of the plurality of concave portions.

* * * * *